United States Patent
Ishibashi et al.

(10) Patent No.: US 12,105,405 B2
(45) Date of Patent: Oct. 1, 2024

(54) CONVERSION LENS ATTACHMENT STRUCTURE, AND INSPECTION DEVICE

(71) Applicant: CASIO COMPUTER CO., LTD., Tokyo (JP)

(72) Inventors: Jumpei Ishibashi, Nishitokyo (JP); Yoshiharu Houjou, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 84 days.

(21) Appl. No.: 17/790,956

(22) PCT Filed: Jan. 12, 2021

(86) PCT No.: PCT/JP2021/000718
§ 371 (c)(1),
(2) Date: Jul. 5, 2022

(87) PCT Pub. No.: WO2021/157293
PCT Pub. Date: Aug. 12, 2021

(65) Prior Publication Data
US 2023/0041101 A1   Feb. 9, 2023

(30) Foreign Application Priority Data
Feb. 3, 2020   (JP) ................. 2020-016631

(51) Int. Cl.
*G03B 17/14*   (2021.01)
*G02B 7/14*   (2021.01)

(52) U.S. Cl.
CPC ............... *G03B 17/14* (2013.01); *G02B 7/14* (2013.01)

(58) Field of Classification Search
None
See application file for complete search history.

(56) References Cited

U.S. PATENT DOCUMENTS 10,537,248 B2 *   1/2020   Hong ................. G02B 25/005
10,678,120 B1 *   6/2020   Lozano-Buhl ............ H01F 7/02
(Continued)

FOREIGN PATENT DOCUMENTS

CN   205670213 U   11/2016
EP   2607953 A1   6/2013
(Continued)

OTHER PUBLICATIONS

Japanese Office Action (and English language translation thereof) dated Jun. 14, 2022, issued in Japanese Application No. 2021-115456.
(Continued)

*Primary Examiner* — Rodney E Fuller
(74) *Attorney, Agent, or Firm* — Holtz, Holtz & Volek PC

(57) ABSTRACT

A conversion lens attachment structure includes a first magnetic body provided on a conversion lens device that includes a conversion lens, and a second magnetic body provided on a device main body that includes a master lens. The conversion lens device is attached to the device main body due to a first surface of the first magnetic body and a second surface of the second magnetic body being pulled toward each other, and the second magnetic body is provided such that a normal line of the second surface is not parallel to an optical axis of the master lens.

11 Claims, 15 Drawing Sheets

(56) References Cited

U.S. PATENT DOCUMENTS

| | | | | |
|---|---|---|---|---|
| 2014/0066727 A1* | 3/2014 | Heine | ............... | A61B 5/0077 600/306 |
| 2015/0036311 A1* | 2/2015 | Mullani | ............... | A61B 5/0077 362/230 |
| 2020/0264404 A1* | 8/2020 | Hanaoka | ............... | G02B 7/021 |
| 2021/0219842 A1* | 7/2021 | Trotzenberg | ............... | F21V 9/06 |
| 2023/0041101 A1 | 2/2023 | Ishibashi et al. | | |

FOREIGN PATENT DOCUMENTS

| | | | | | |
|---|---|---|---|---|---|
| EP | 3818926 A1 | * | 5/2021 | ........... | A61B 5/0059 |
| JP | 3096603 U | | 9/2003 | | |
| JP | 2004317955 A | | 11/2004 | | |
| JP | 2008076917 A | | 4/2008 | | |
| JP | 2013029558 A | * | 2/2013 | | |
| JP | 2015188590 A | | 11/2015 | | |
| JP | 2018005155 A | | 1/2018 | | |
| JP | 3220020 U | | 2/2019 | | |
| JP | 2019105704 A | | 6/2019 | | |
| JP | 2021124561 A | | 8/2021 | | |
| KR | 20130019695 A | | 2/2013 | | |

OTHER PUBLICATIONS

International Search Report (ISR) (and English language translation thereof) dated Mar. 30, 2021, issued in International Application No. PCT/JP2021/000718.
Japanese Office Action (and English language translation thereof) dated Mar. 23, 2021, issued in Japanese Application No. 2020-016631.
Written Opinion dated Mar. 30, 2021, issued in International Application No. PCT/JP2021/000718.
Japanese Office Action (and an English language translation thereof) dated Mar. 26, 2024, issued in counterpart Japanese Application No. 2023-021275.
Extended European Search Report (EESR) dated Feb. 26, 2024, issued in counterpart European Application No. 21751011.4.
Australian Examination Report dated Jul. 16, 2024, issued in counterpart Australian Application No. 2023226734.

* cited by examiner

CONVERSION LENS ATTACHMENT STRUCTURE, AND INSPECTION DEVICE

TECHNICAL FIELD

The present disclosure relates to a conversion lens attachment structure and an inspection device.

BACKGROUND ART

Various structures have been proposed for conversion lens attachment structures that are attached to device main bodies. For example, Patent Literature 1 describes a structure for attaching a conversion lens to a mobile phone by a magnet, provided on a conversion lens device that includes a conversion lens, being attracted to a metal piece provided on a surface of the mobile phone.

CITATION LIST

Patent Literature

Patent Literature 1: Registered Japanese Utility Model No. 3096603

SUMMARY OF INVENTION

Technical Problem

With the mobile phone described in Patent Literature 1, the metal piece that is attracted to the magnet is provided so as to be orthogonal to the optical axis of the camera. As such, a region of a size equal to the planar dimensions of the metal piece must be secured as the region for providing the metal piece, and a metal piece of a certain size is required to obtain a certain magnitude of attractive force of the magnet to prevent the conversion lens from falling off. Due to this, with conventional attachment structures, the portion of the mobile phone where the conversion lens is to be attached is comparatively large.

The present disclosure is made with the view of the above situation, and an objective of the present disclosure is to provide a conversion lens attachment structure and an inspection device whereby holding strength of the conversion lens to a device main body can be suitably obtained and, also, the structure for attaching the conversion lens can be made compact.

Solution to Problem

A conversion lens attachment structure includes: a first magnetic body provided on a conversion lens device that includes a conversion lens; and a second magnetic body provided on a device main body that includes a master lens; wherein the conversion lens device is held in a state attached to the device main body due to an attraction effect between a first surface of the first magnetic body and a second surface of the second magnetic body, and the second magnetic body is provided such that a normal line of the second surface is not parallel to an optical axis of the master lens.

Advantageous Effects of Invention

According to the present disclosure, it is possible to provide a conversion lens attachment structure and an inspection device whereby holding strength of a conversion lens to a device main body can be suitably obtained and, also, the structure for attaching the conversion lens can be made compact.

DESCRIPTION OF EMBODIMENTS

Hereinafter, embodiments of the present disclosure are described while referencing the drawings. Note that, to facilitate comprehension of the embodiments, a description is given while appropriately referencing a Cartesian coordinate system illustrated in FIG. 1. An X-axis direction and a Y-axis direction in this Cartesian coordinate system are orthogonal to an optical axis OA1 (FIG. 5) of a master lens 20 and an optical axis OA2 (FIG. 8) of a conversion lens 110, which are described later. A Z-axis direction in the Cartesian coordinate system is parallel to the optical axis OA1 of the master lens 20 and the optical axis OA2 of the conversion lens 110.

Note that, in the present description, the terms "dermoscope" and "dermoscopy" are used to refer respectively to a skin examination magnifier (device) and skin examination by a magnifier or a use of a magnifier (action), in a manner similar to the usage of "microscope" (device) and "microscopy" (examination by a microscope or use of a microscope (method)).

Overview of Inspection Device 1

Figure 1:
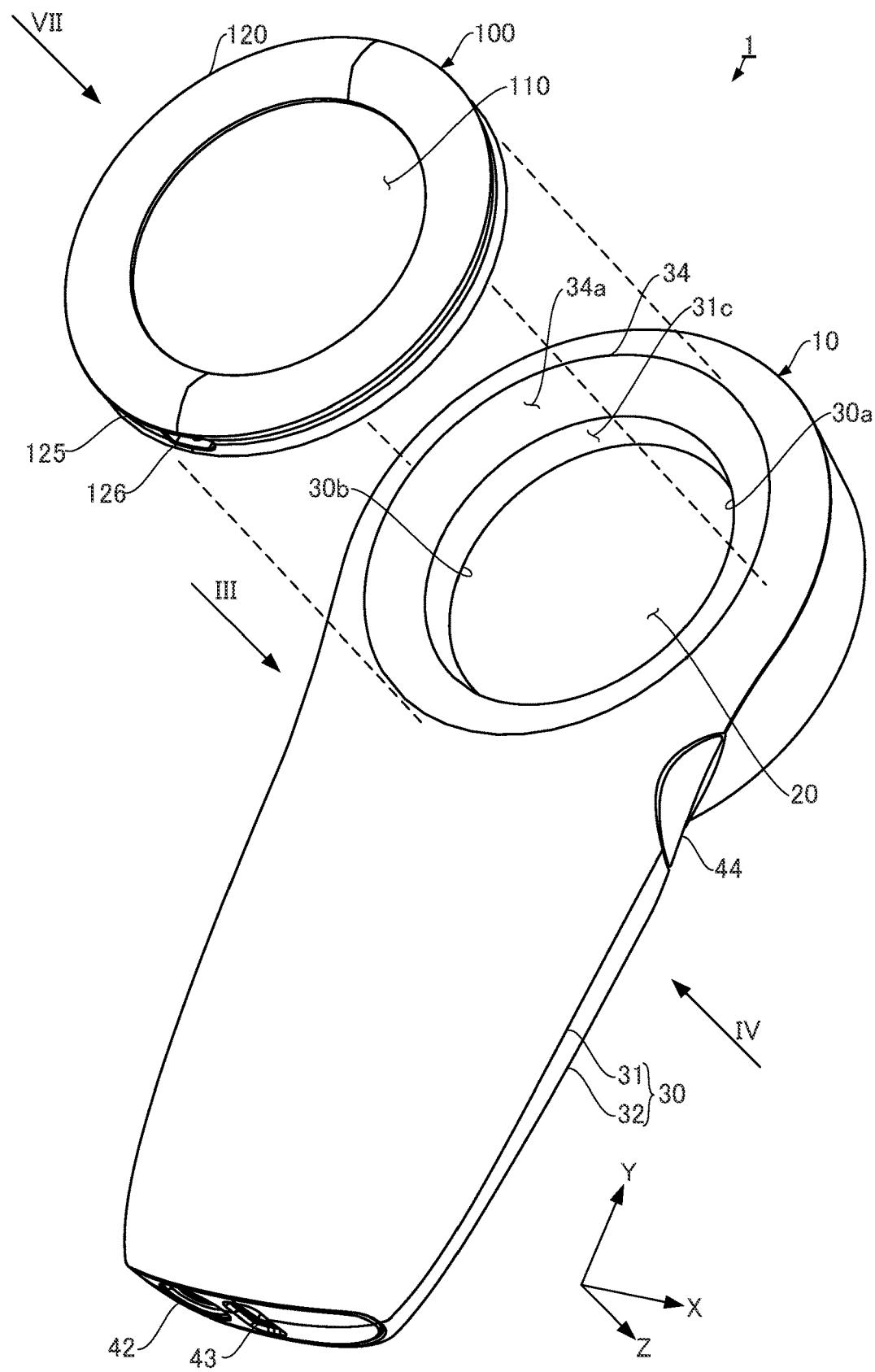
FIG. 1 is a drawing illustrating an inspection device according to an embodiment of the present disclosure, and is a perspective view of a state in which a conversion lens device is detached.
Figure 2:
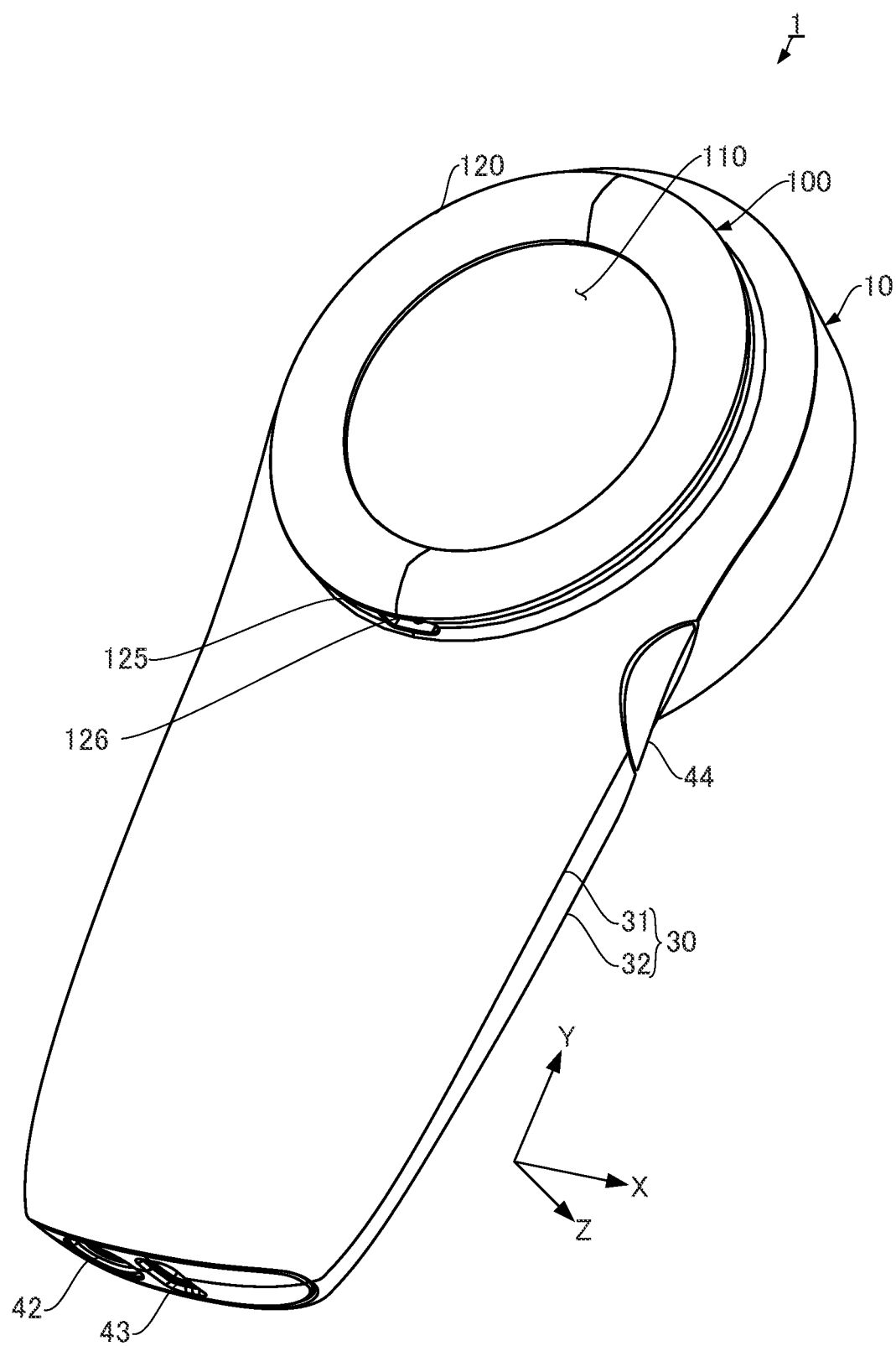
FIG. 2 is a drawing illustrating the inspection device according to the embodiment of the present disclosure, and is a perspective view of a state in which the conversion lens device is attached.

An inspection device 1 is a dermoscope that has skin as an object to be inspected. As illustrated in FIGS. 1 and 2, the inspection device 1 includes a device main body 10, and a conversion lens device 100 that is attachable/detachable to/from a surface on the −Z-axis direction side of the device main body 10. As illustrated in FIG. 1, in a state in which the conversion lens device 100 is detached (a first state), a user can perform, through the circular master lens 20 provided on the device main body 10, a dermoscopy inspection of skin arranged on the +Z-axis direction side. Meanwhile, as illustrated in FIG. 2, in a state in which the conversion lens device 100 is attached to the device main body 10 (a second state), the user can perform, through the master lens 20 and a circular conversion lens 110 provided on the conversion lens device 100, a dermoscopy inspection of skin arranged on the +Z-axis direction side. The master lens 20 and the conversion lens 110 are magnification lenses. The user can observe skin magnified to a desired size by appropriately changing the state of the inspection device 1 between the first state and the second state.

Configuration of Device Main Body 10

Figure 3:
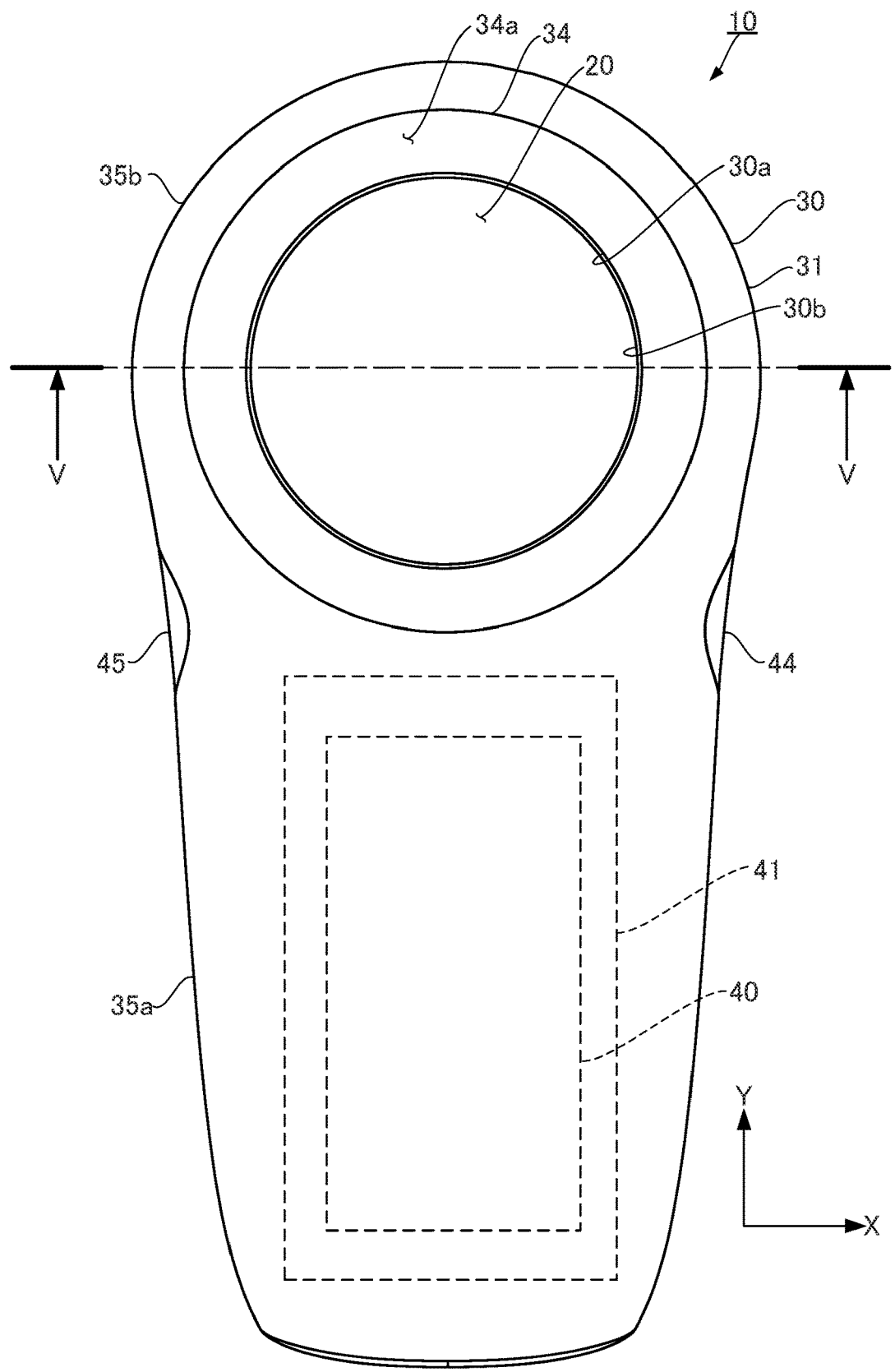
FIG. 3 is a front view of a device main body, viewed from arrow III of FIG. 1.
Figure 4:
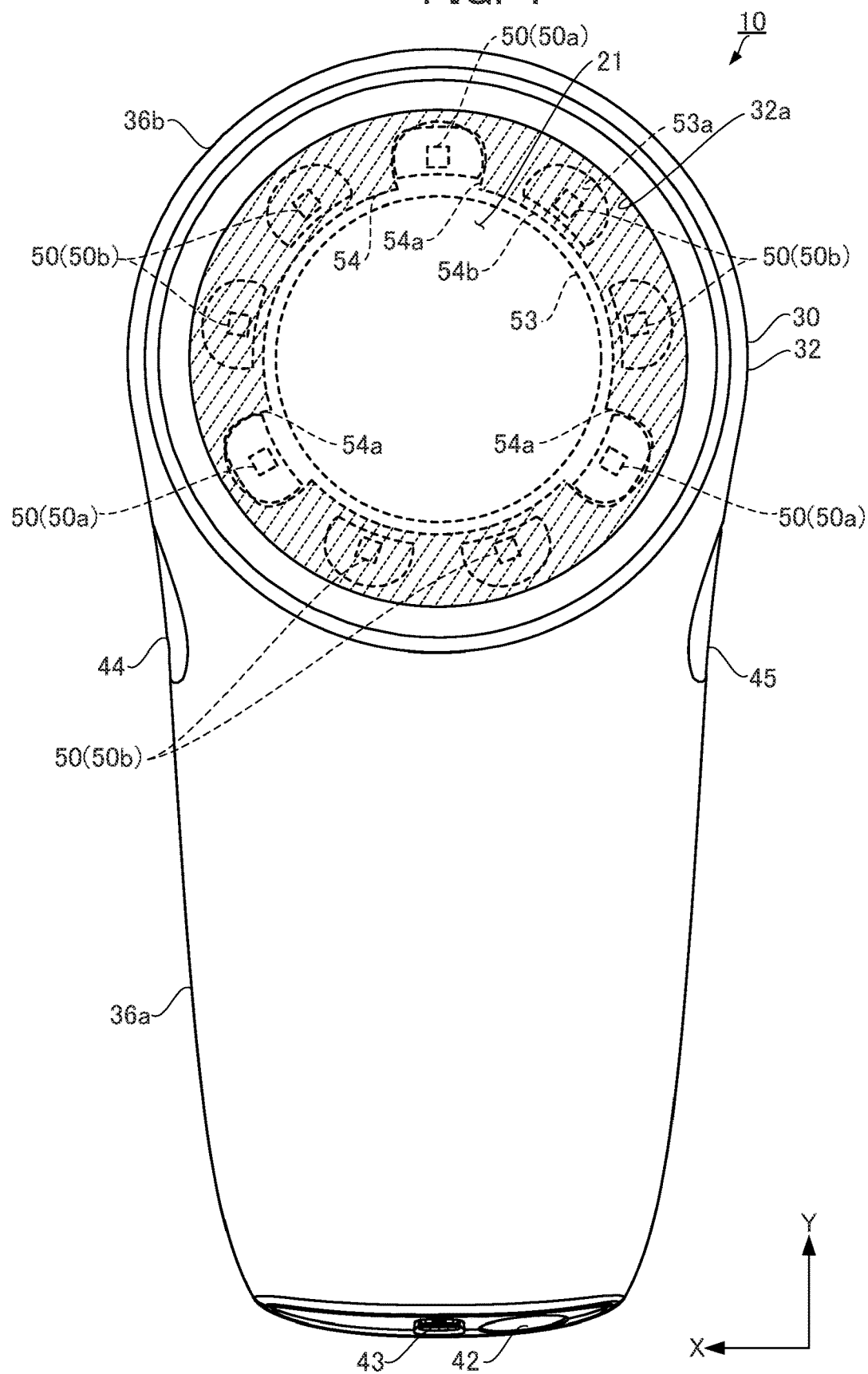
FIG. 4 is a back view of the device main body, viewed from arrow IV of FIG. 1.

As illustrated in FIGS. 1 and 2, the device main body 10 includes a case body 30 that is constituted by combining a first case 31 provided on the-Z-axis side and a second case 32 provided on the +Z side with each other. In one example, the first case 31 and the second case 32 are formed from a white synthetic resin. As illustrated in FIG. 3, the first case 31 has a planar shape such as that obtained by combining an expanding section 35a that has a width that increases toward the +Y-axis direction side, and a semicircular semicircle section 35b. A circular opening 30b is formed in the first case 31, at a connection between the expanding section 35a and the semicircle section 35b. As illustrated in FIG. 4, the second case 32 has a planar shape such as that obtained by combining an expanding section 36a that has a width that increases toward the +Y-axis direction side, and a semicircular semicircle section 36b. A circular opening 32a is formed in the second case 32, at a connection between the expanding section 36a and the semicircle section 36b. The opening 32a formed in the second case 32 is larger than the opening 30b formed in the first case 31.

A non-illustrated housing space for housing various types of articles is formed between the first case 31 and the second case 32. For example, as illustrated in FIG. 3, a rechargeable battery 40, and a circuit board 41 electrically connected to various electronic components are housed in the housing space of the case body 30. The battery 40 supplies electricity to the various electronic components of the inspection device 1.

As illustrated in FIG. 1, the master lens 20, which closes the opening 30b, is provided on the case body 30. As illustrated in FIG. 4, a cover plate 21 is provided on the case body 30 so as to close the opening 32a.

As illustrated in FIGS. 1 and 2, a charging terminal 42 used when charging the battery 40, and a strap attacher 43 having a hole for passing a strap (non-illustrated) through are provided on an end surface on the-Y-axis direction side of the case body 30.

As illustrated in FIGS. 3 and 4, on the case body 30, a power button 44 is provided on a side surface on the +X-axis direction side, and a switch button 45 that is press-operated when switching a light source that emits light is provided on a side surface on the-X-axis direction side.

Figure 6:
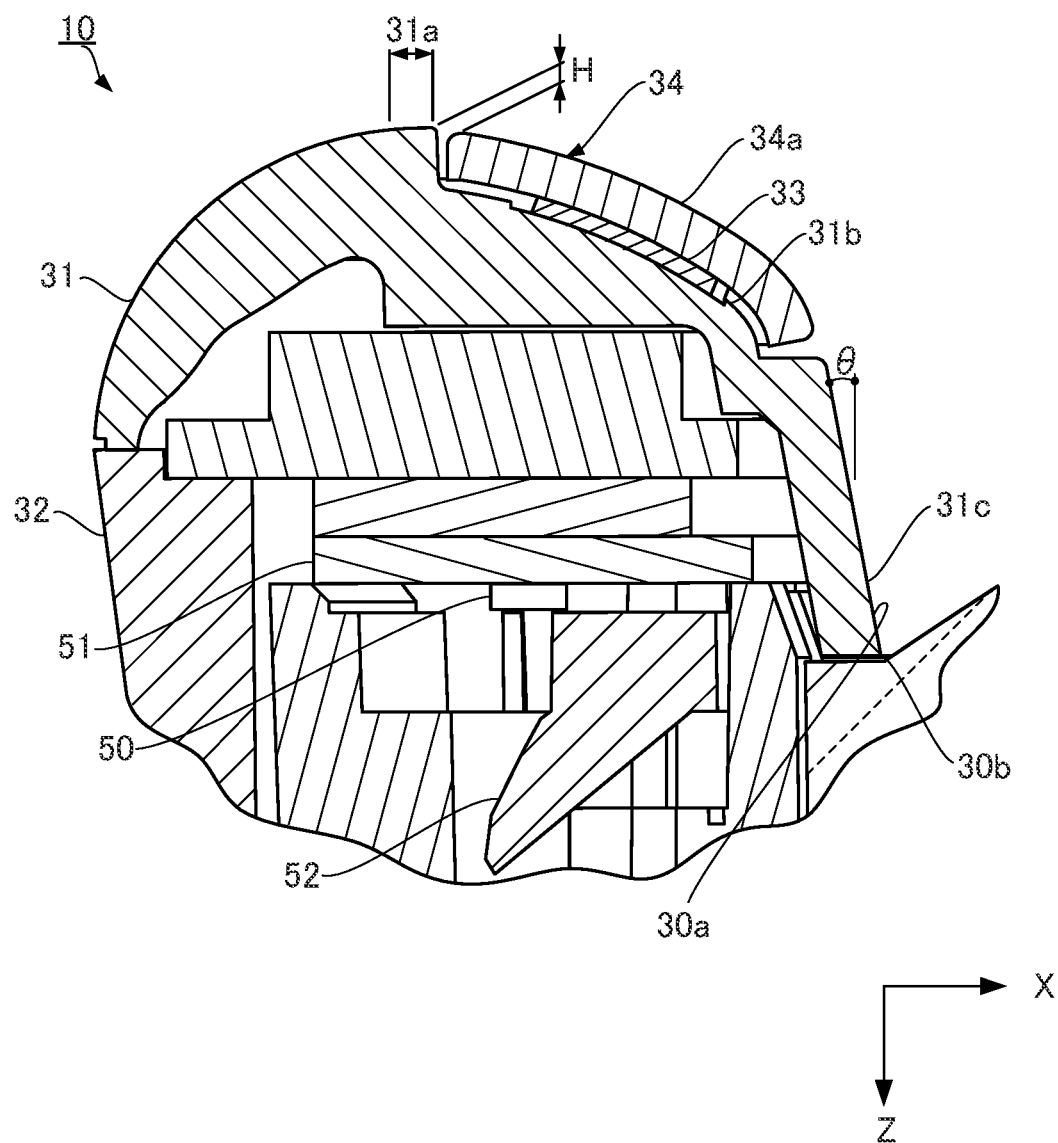
FIG. 6 is an enlarged view of portion "VP" of FIG. 5.
Figure 8:
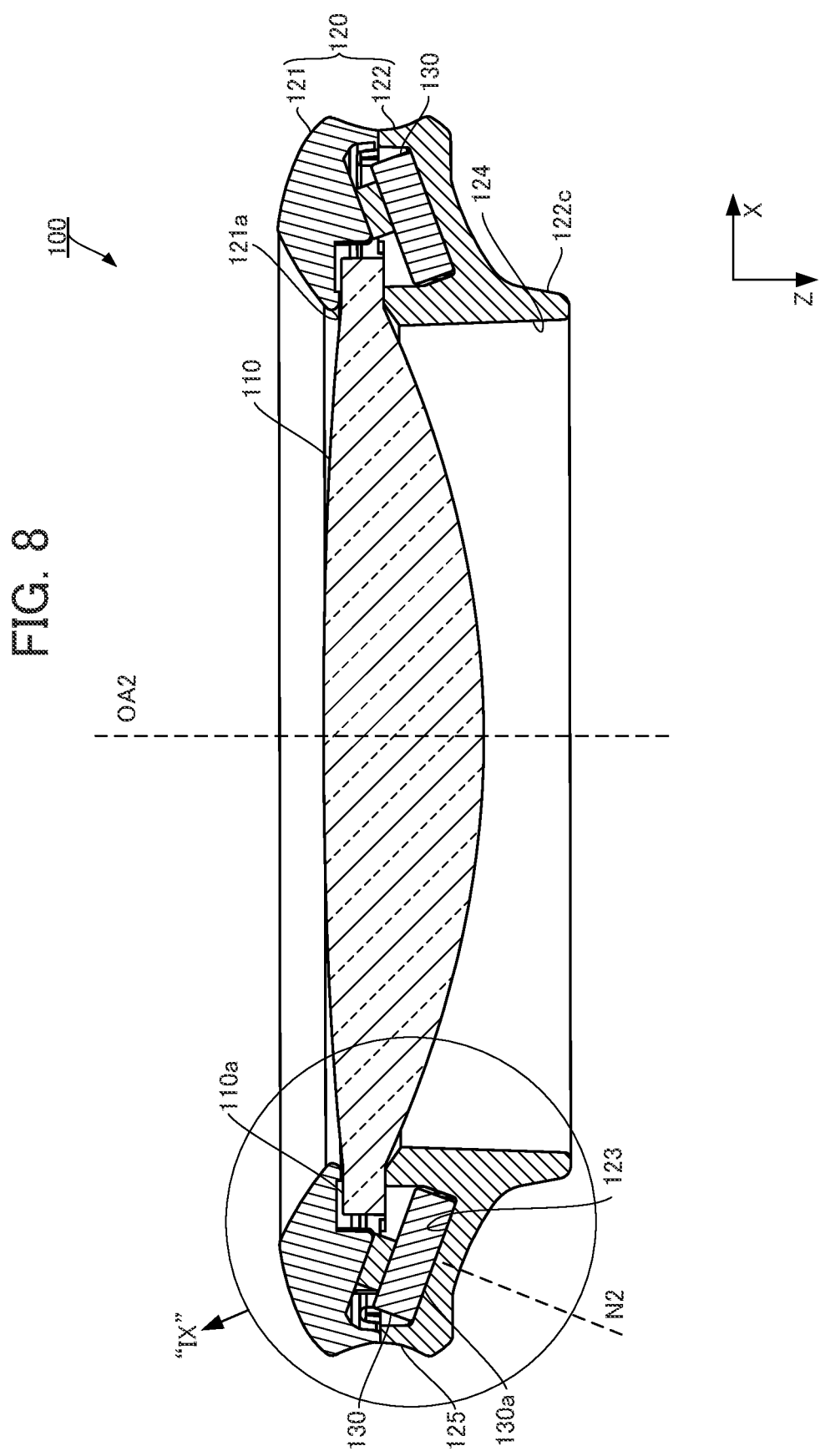
FIG. 8 is a cross-sectional view of the conversion lens device, cut along cross-section line VIII-VIII of FIG. 7.

As illustrated in FIG. 6, a contact surface 31a, an inclined surface 31b, and an inclined wall 31c are formed in order from the outside around the opening 30b of the first case 31. The contact surface 31a is a region that contacts the conversion lens device 100 illustrated in FIG. 1. The contact surface 31a is subjected to surface texturing, and a fine pattern formed on a surface of a mold is transferred thereto when molding. The inclined surface 31b is a location that is stepped down from the contact surface 31a. The inclined surface 31b is a surface gradually formed in the +Z direction from the contact surface 31a toward the inclined wall 31c, and is a surface that is inclined with respect to the X-Y plane. The inclined wall 31c is inclined at an angle θ with respect to the Z-axis direction. The inclined wall 31c is formed in a cylindrical shape that penetrates in the Z-axis direction, and is formed such that the diameter thereof increases in the-Z-axis direction. The opening 30b of the first case 31 is formed at an end on the +Z-axis side of the inclined wall 31c. The degree of inclination of the inclined wall 31c with respect to the X-Y plane is larger than the degree of inclination of the inclined surface 31b with respect to the X-Y plane. The inclined wall 31c defines a portion of an insertion part 30a into which a cylindrical protrusion 122c, provided on the conversion lens device 100 illustrated in FIG. 8, is inserted. A metal piece 34 as a second magnetic body is adhered to the inclined surface 31b by double-sided tape 33.

Figure 5:
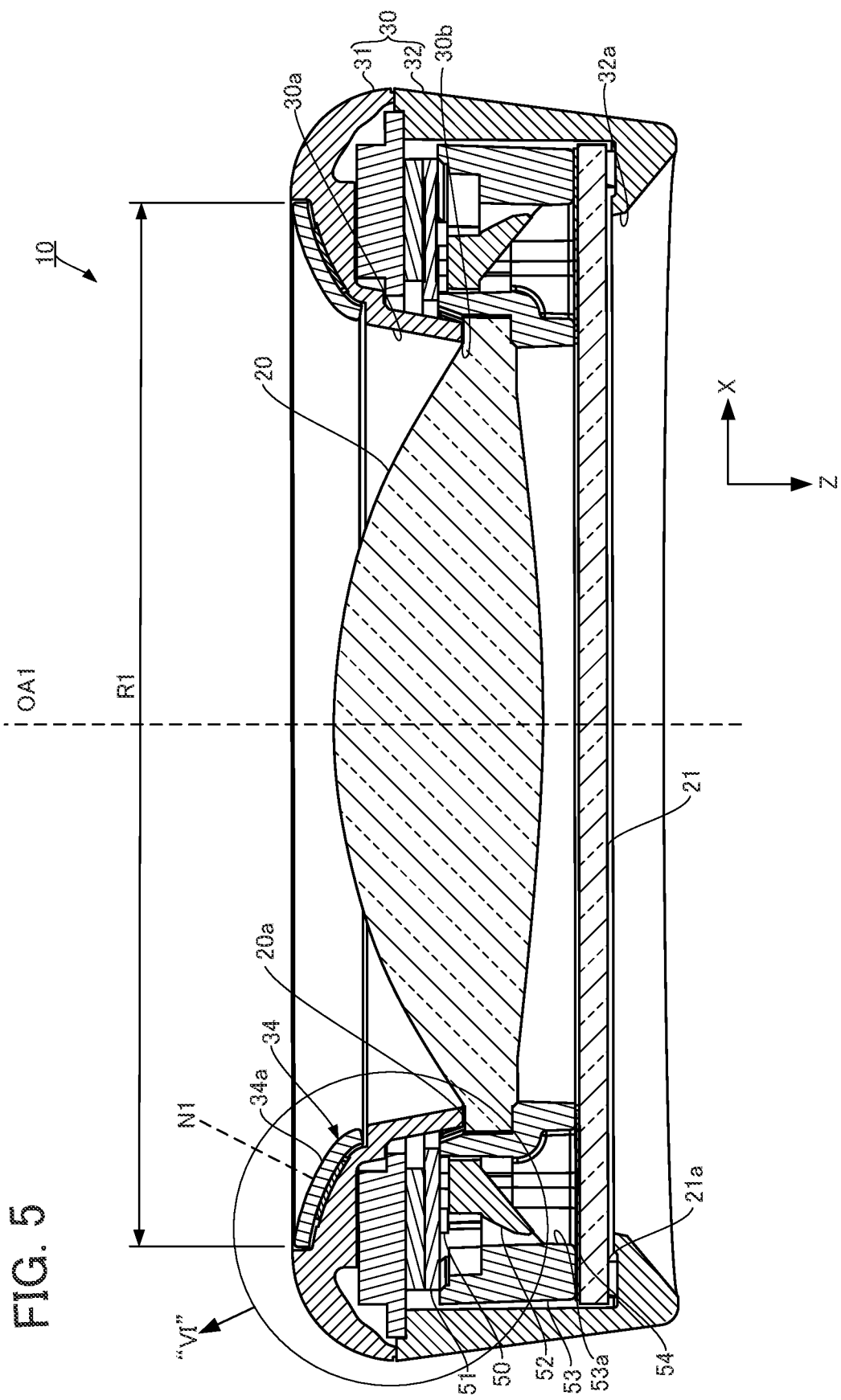
FIG. 5 is a cross-sectional view of the device main body, cut along cross-section line V-V of FIG. 3.

The metal piece 34 is formed from a magnetic body that is attracted to a permanent magnet. For example, the metal piece 34 is formed from stainless steel. As illustrated in FIG. 6, the metal piece 34 has a shape that corresponds to the shape of the inclined surface 31b. Specifically, as illustrated in FIGS. 1 and 5, the metal piece 34 is formed in a cylindrical shape that penetrates in the Z-axis direction, and is formed such that the diameter thereof increases in the-Z-axis direction. As such, as illustrated in FIG. 5, a main surface 34a of the metal piece 34 is inclined. A normal line N1 of the main surface 34a is directed in a direction approaching the optical axis OA1 of the master lens 20 that extends in the Z-axis direction, instead of parallel to the optical axis OA1. Note that, although the angle of inclination of the main surface 34a varies by surface position, the direction in which the normal line thereof extends at any surface position is not parallel to the optical axis OA1 of the master lens 20. Additionally, a step H is formed at a location where the contact surface 31a of the case body 30 is adjacent to the main surface 34a of the metal piece 34, and the main surface 34a of the metal piece 34 is positioned recessed more to the +Z-axis side than the contact surface 31a.

The master lens 20 is a magnification lens that has a magnification factor of about 6-times. As illustrated in FIG. 5, an outer periphery 20a of the master lens 20 is sandwiched between the first case 31 and a housing 53 (described later). In one example, the cover plate 21 is formed from transparent synthetic resin, and is formed in a disk shape. An outer periphery 21a of the cover plate 21 is sandwiched between the second case 32 and the housing 53 (described later). The cover plate 21 covers the master lens 20 from the +Z-axis side. When performing a dermoscopy inspection, the skin that is more to the +Z-axis direction side than the device main body 10 is magnified by the master lens 20 and observed by the user through the master lens 20 and the cover plate 21.

A LED substrate 51 on which a light emitting diode (LED) 50 for irradiating the skin with light is mounted, a light guide 52 that guides the light emitted from the LED 50 in a direction approaching the optical axis OA1, the housing 53 in which the LED 50 and the light guide 52 are housed, and a polarizing plate 54 that polarizes the light from the LED 50 are provided around the master lens 20 of the case body 30.

The LED substrate 51 is a substrate that is formed in a ring shape so as to surround the master lens 20. As illustrated in FIG. 4, nine LEDs 50 are arranged on the LED substrate 51 at equal intervals along the circumferential direction. The nine LEDs 50 are arranged around the master lens 20, and act as a ring flash that emits light from a peripheral position. The nine LEDs 50 emit visible light in the +Z-axis direction. The emitted light enters the light guide 52, and is emitted having a direction of travel that is directed in the direction approaching the optical axis OA1 of the master lens 20. As a result, the region of the skin observed in the center of the master lens 20 can be irradiated with light, and the skin that is the object to be inspected can be uniformly irradiated with light.

As illustrated in FIG. 4, the housing 53 includes, at positions corresponding to each of the nine LEDs 50, an opening 53a that penetrates in the Z-axis direction. The light from the LEDs 50 is emitted through these openings 53a, Note that, in FIG. 4, to ensure the ease of viewing of the drawing, only one location is marked with the reference numeral of the opening 53a, and the reference numerals of the other openings 53a are omitted.

As illustrated in FIG. 5, the polarizing plate 54 is interposed between the cover plate 21 and the housing 53. In FIG. 4, to make the details of the polarizing plate 54 understandable, the polarizing plate 54 is indicated by a dashed line and the region of the polarizing plate 54 is marked with hatching. As such, the hatching used to mark the polarizing plate 54 in FIG. 4 does not represent cross-sections. The polarizing plate 54 is formed in a ring shape corresponding to the LED substrate 51, and includes three notches 54a formed from an inner edge 54b. The three notches 54a are arranged at equal intervals along the circumferential direction of the polarizing plate 54, and are formed so as to open the +Z-axis direction side of the corresponding LEDs 50. Specifically, three of the nine arranged LEDs 50 are not covered by the polarizing plate 54 and are used as LEDs 50a for emitting visible light, and the remaining six of the nine arranged LEDs 50 are covered by the polarizing plate 54 and are used as LEDs 50b that emit polarized light. Note that the amount of light, of the light from the LEDs 50b covered by the polarizing plate 54, decreases as a result of passing through the polarizing plate 54. Accordingly, more of the LEDs 50b for emitting polarized light are provided than the LEDs 50a for emitting visible light.

Note that, at a time of dermoscopy inspection, it is possible to select whether to irradiate the skin with visible light or irradiate the skin with polarized light by press-operating the switch button 45 illustrated in FIG. 3 and the like. For example, when the power button 44 is pressed to turn the power of the inspection device 1 ON, a first light emission state is achieved in which the LEDs 50a emit visible light but the LEDs 50b do not emit polarized light. When the switch button 45 is pressed once, the state changes from the first light emission state to a second light emission state in which the LEDs 50a turn OFF and do not emit visible light and the LEDs 50b turn ON and emit polarized light. Thus, each time the switch button 45 is press-operated, the emission state of the light switches between the first light emission state and the second light emission state.

Configuration of Conversion Lens Device 100

Next, the configuration of the conversion lens device 100 that attaches/detaches to/from the device main body 10 is described. As illustrated in FIGS. 1 and 2, the conversion lens device 100 includes the conversion lens 110, and a lens frame 120 that holds the outer periphery of the conversion lens 110 and in which a permanent magnet 130 (FIG. 8) as a first magnetic body is provided.

The conversion lens 110 is a magnification lens that can be combined with the master lens 20 illustrated in FIG. 1 to obtain a magnification factor of about 9-times.

As illustrated in FIG. 8, the lens frame 120 includes a first case 121 provided on the -Z-axis side, and a second case 122 that is provided on the +Z side and that combines with the first case 121. In one example, the lens frame 120 is formed from white synthetic resin. A circular opening 121a penetrating in the Z-axis direction is formed in the center of the first case 121. A circular opening 124 penetrating in the Z-axis direction is formed in the center of the second case 122. The first case 121 and the second case 122 are combined by matching the center of the circular opening 121a and the center of the circular opening 124 with each other. When combined in this manner, the first case 121 and the second case 122 grip an outer periphery 110a of the conversion lens 110 that is provided so as to close the opening 121a and the opening 124. As a result, the conversion lens 110 is held by the lens frame 120. As illustrated in FIGS. 1 and 2, a strap attacher 126 having a hole for passing a strap (non-illustrated) therethrough is provided on a side surface (surface on the X-Z plane) of the lens frame 120. Additionally, an indentation 125 having a recessed center side extends in the circumferential direction on the side surface of the lens frame 120. A finger of the user can easily catch on the indentation 125 and, as a result, the indentation 125 can facilitate the handling of the conversion lens device 100.

Figure 7:
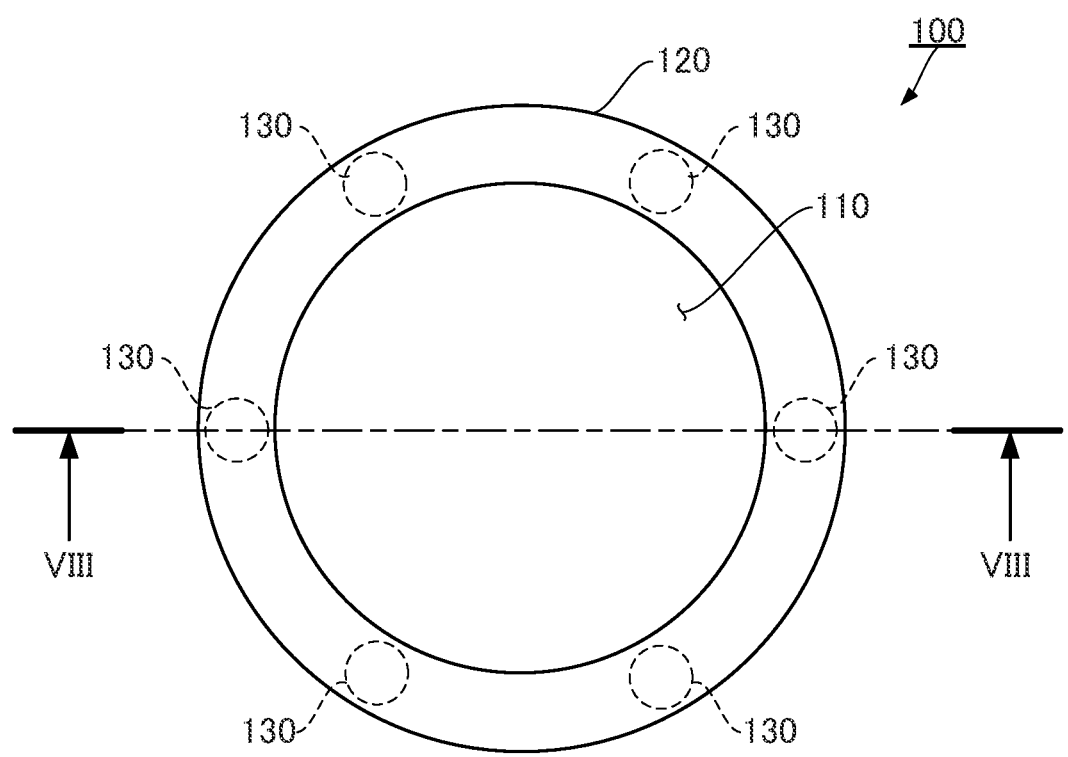
FIG. 7 is a front view of the conversion lens device, viewed from arrow VII of FIG. 1.

As illustrated in FIGS. 7 and 8, the permanent magnet 130 is formed in a cylindrical shape, and six of the permanent magnet 130 are arranged at equal intervals in the circumferential direction of the conversion lens 110. As illustrated in FIG. 8, the permanent magnet 130 is attached to the inclined surface 123, that is inclined with respect to the X-Y plane, of the second case 122. The permanent magnet 130 that is attached to the inclined surface 123 in this manner is arranged such that, when the conversion lens device 100 is attached to the device main body 10, the main surface 130a of the permanent magnet 130 is substantially parallel to at least a portion of the main surface 34a of the metal piece 34 illustrated in FIG. 5. As such, the permanent magnet 130 is arranged such that a normal line N2 of the main surface 130a of the permanent magnet 130 is not parallel to the optical axis OA2 of the conversion lens 110.

Figure 9:
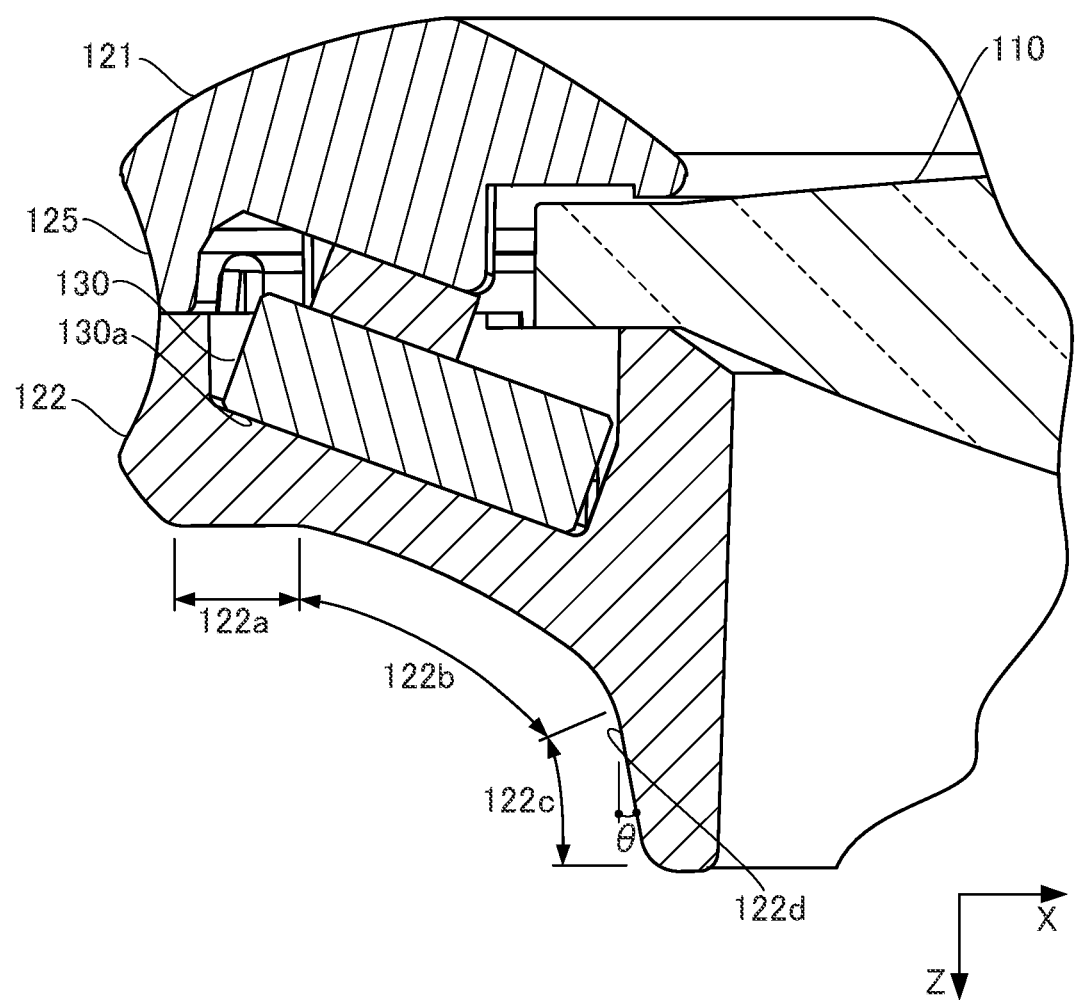
FIG. 9 is an enlarged view of portion "IX" of FIG. 8.

As illustrated in FIG. 9, the second case 122 includes, on a portion of the +Z-axis side thereof, a contactor 122a that contacts the contact surface 31a of the first case 31 illustrated in FIG. 6, a contact avoider 122b curved inwardly (to the side approaching the optical axis OA2) from the contactor 122a toward the +Z axis direction side, and a cylindrical protrusion 122c that is inserted into the insertion part 30a of the case body 30 when the conversion lens device 100 is attached to the device main body 10.

The contactor 122a is constituted from a plane (a plane extending the X-Y direction) orthogonal to the optical axis OA2 of the conversion lens 110 illustrated in FIG. 8, and is a plane region formed in a ring shape along the outer periphery of the second case 122. The protrusion 122c protrudes to the +Z-axis direction side from the contact avoider 122b, and an outer peripheral surface 122d of the protrusion 122c is inclined at an angle θ with respect to the Z-axis direction. The angle θ is the same as the angle θ of the inclined wall 31c with respect to the Z-axis direction illustrated in FIG. 6. Specifically, the outer peripheral surface 122d of the protrusion 122c and the inclined wall 31c illustrated in FIG. 6 are inclined in the same direction and at the same angle. Additionally, the outer diameter of the protrusion 122c is, for example, 1 mm smaller than the inner diameter of the insertion part 30a.

Configuration of Inspection Device 1 to Which Conversion Lens Device 100 is Attached At the time of dermoscopy inspection, the conversion lens device 100 is attached to the device main body 10 when inspecting the skin magnified at a higher magnification factor than the magnification factor of the master lens 20. At this time, the protrusion 122c of the conversion lens device 100 is inserted into the insertion part 30a of the device main body 10. The outer diameter of the protrusion 122c and the inner diameter of the insertion part 30a have substantially the same dimensions and, due to this, rattling of the conversion lens device 100 in the X-Y plane direction is suppressed. At this time, the metal piece 34 provided on the device main body 10 and the permanent magnet 130 provided on the conversion lens device 100 are brought close to each other. As a result, the main surface 130a as the first surface of the permanent magnet 130 and the main surface 34a as the second surface of the metal piece 34 are pulled toward each other. Due to this, the conversion lens device 100 is attracted to the device main body 10 due to magnetic force, and is attached to and held to the device main body 10.

Figure 11:
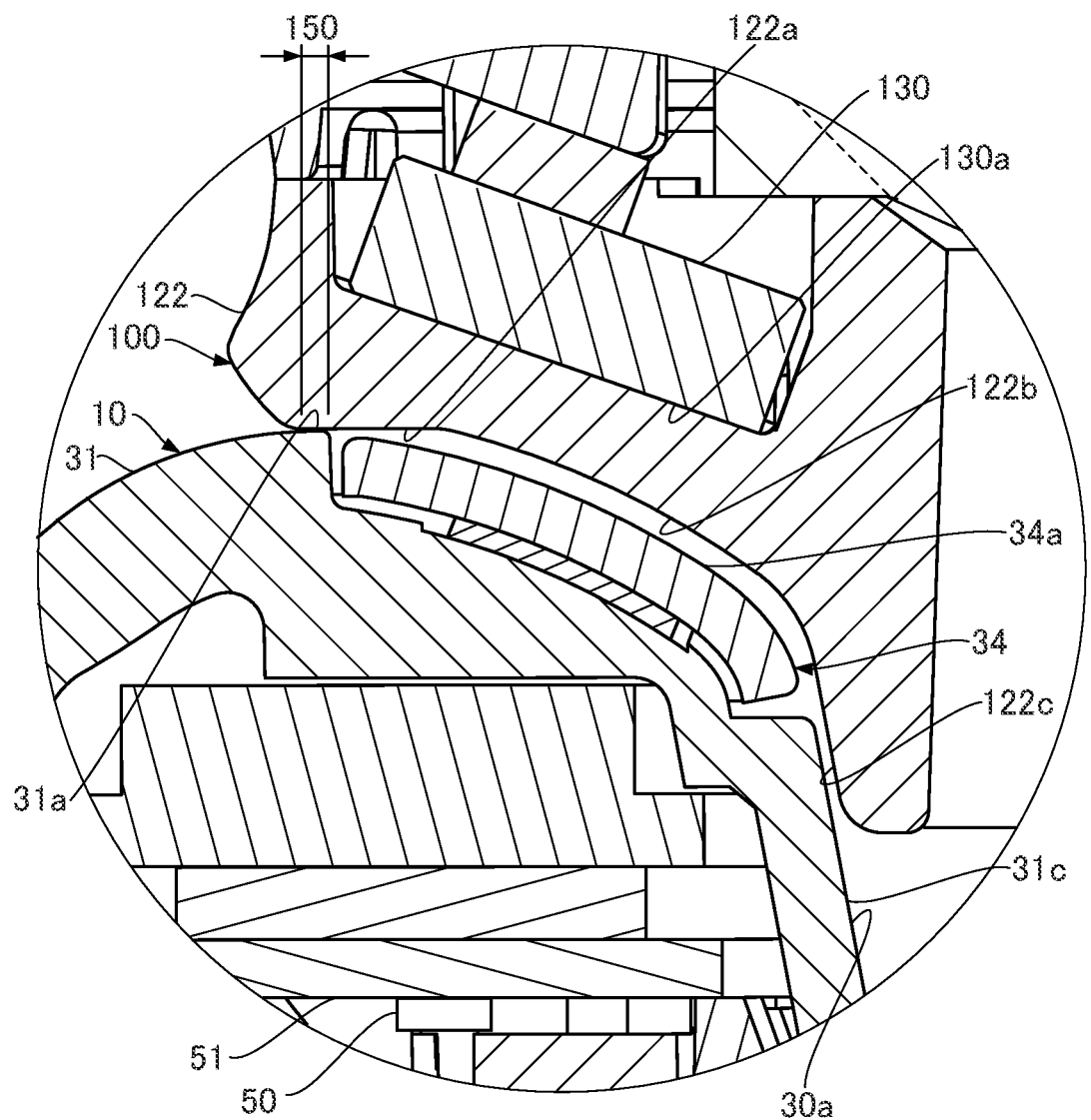
FIG. 11 is an enlarged view of portion "XI" of FIG. 10.

At this time, as illustrated in FIG. 11, when the metal piece 34 and the permanent magnet 130 are pulled toward each other, the device main body 10 and the conversion lens device 100 are brought into tight close contact with each other in a limited region called a contact region 150. As described above, the contact region 150 is a ring shaped region that is formed so as to surround the master lens 20 and the conversion lens 110. As a result, malfunctions such as the conversion lens device 100 falling off during inspection can be prevented.

Note that, as illustrated in FIG. 6, the step H is provided between the main surface 34a of the metal piece 34 and the contact surface 31a of the first case 31, and the contact surface 31a is positioned slightly more to the-Z-axis direction side than the main surface 34a. Additionally, as illustrated in FIG. 11, the contact avoider 122b of the second case 122 is formed in a curved shape so as to avoid contact with the metal piece 34. Thus, a gap is formed between the conversion lens device 100 and the metal piece 34, and contact between the conversion lens device 100 and the metal piece 34 is avoided.

The conversion lens device 100 can be correctly attached to the device main body 10 by inserting the protrusion 122c of the conversion lens device 100 into the insertion part 30a of the device main body 10. That is, the protrusion 122c and the insertion part 30a act as positioning means of the conversion lens device 100. Shifting of the conversion lens device 100 with respect to the device main body 10 on the X-Y plane can be prevented by the protrusion 122c contacting the insertion part 30a, even when a force acts on the conversion lens device 100 from a direction parallel to the X-Y plane. Specifically, the protrusion 122c and the insertion part 30a act as movement limiting means that limit movement parallel to the X-Y plane of the conversion lens device 100.

Use Method of Inspection Device 1

Figure 12A:
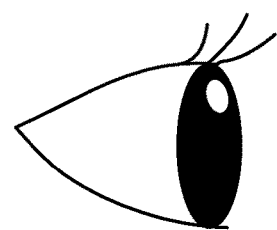
FIG. 12A is a drawing illustrating a situation in which the inspection device according to the embodiment of the present disclosure is being used with the conversion lens device detached, and is a schematic view illustrating a state of visible light exiting.
Figure 12A:
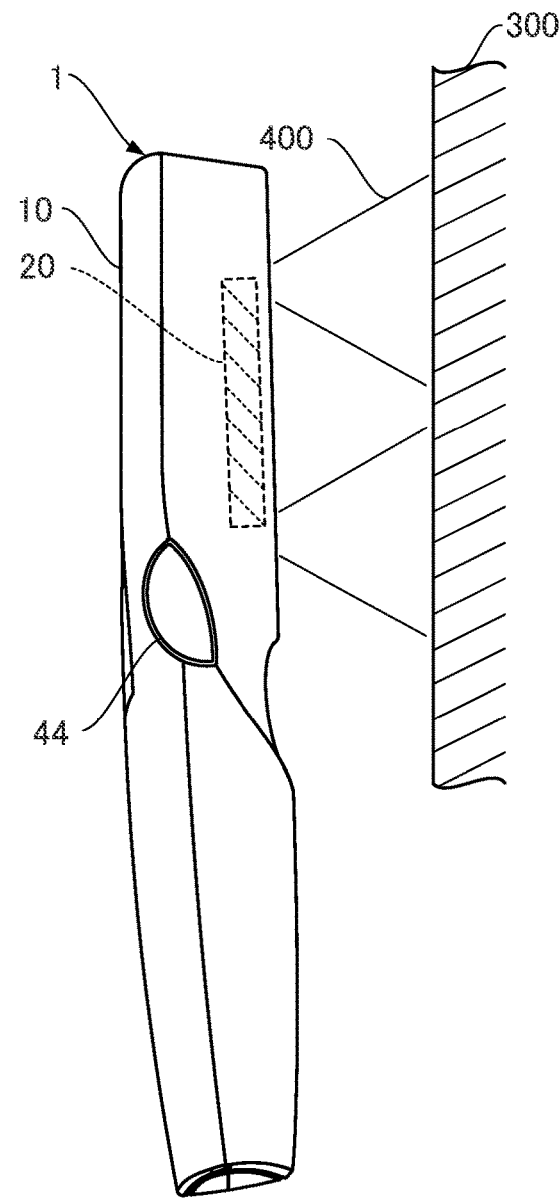
Figure 12B:
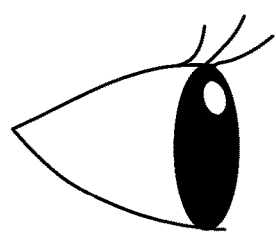
FIG. 12B is a drawing illustrating a situation in which the inspection device according to the embodiment of the present disclosure is being used with the conversion lens device detached, and is a schematic view illustrating a state of polarized visible light exiting.
Figure 12B:
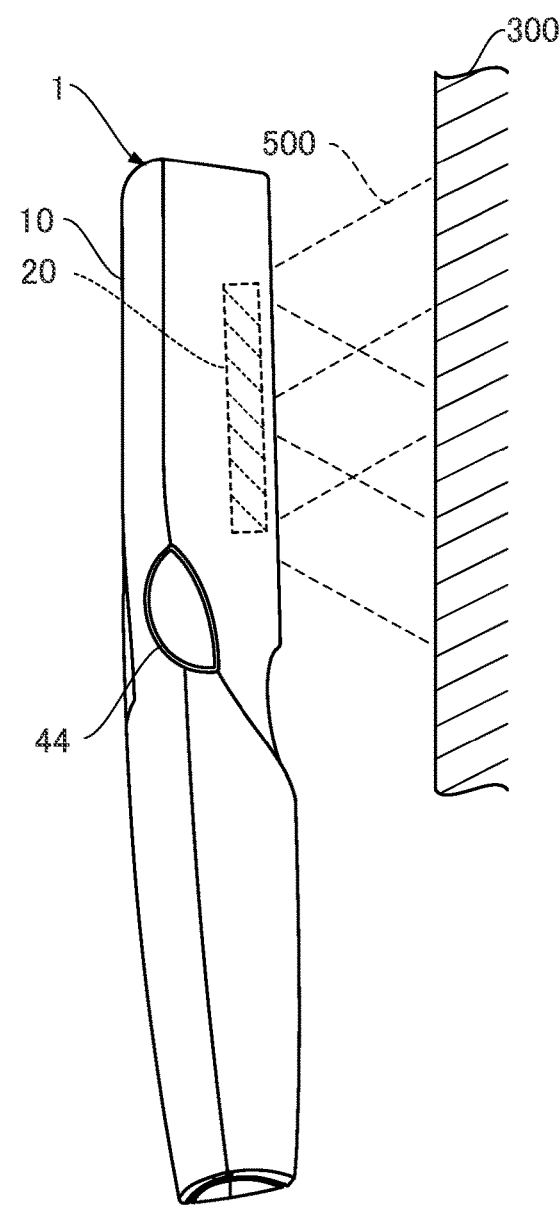

Next, a method for executing dermoscopy inspection using the inspection device 1 is described. When performing a dermoscopy inspection in which the skin that is the object to be inspected is magnified by about six-times, as illustrated in FIGS. 12A and 12B, the inspection is performed using the inspection device 1 with the conversion lens device 100 detached. Firstly, the user press-operates the power button 44 to turn the power of the inspection device 1 ON, and cause visible light 400 to be emitted from the inspection device 1. Of the light sources provided on the inspection device 1, the light sources that emit the visible light 400 are the three LEDs 50a illustrated in FIG. 4. Then, the user brings the inspection device 1 close to the skin 300 and irradiates the skin 300 with the visible light 400. Then, as illustrated in FIG. 12A, the user secures a suitable distance between the skin 300 and the inspection device 1, and observes the skin 300 that is irradiated with the visible light 400. Thus, the user can observe, through the master lens 20, the condition of the magnified stratum corneum on the surface side of the skin 300.

When the inspection of the skin 300 using the visible light 400 is complete, next, the user presses the switch button 45 illustrated in FIG. 3, and switches the light source that emits the light. As a result, polarized visible light 500 is emitted from the inspection device 1. Of the light sources provided on the inspection device 1, the light sources that emit the polarized visible light 500 are the six LEDs 50b and the polarizing plate 54 illustrated in FIG. 4. Then, the user brings the inspection device 1 close to the skin 300 and irradiates the skin 300 with the polarized visible light 500. Then, as illustrated in FIG. 12B, the user secures a suitable distance between the skin 300 and the inspection device 1, and observes the skin 300 that is irradiated with the polarized visible light 500. Thus, the user can observe, through the master lens 20, the conditions of the epidermis and the superficial dermis, which are deeper than the stratum corneum on the surface side, of the skin 300 in a magnified state.

Figure 13A:
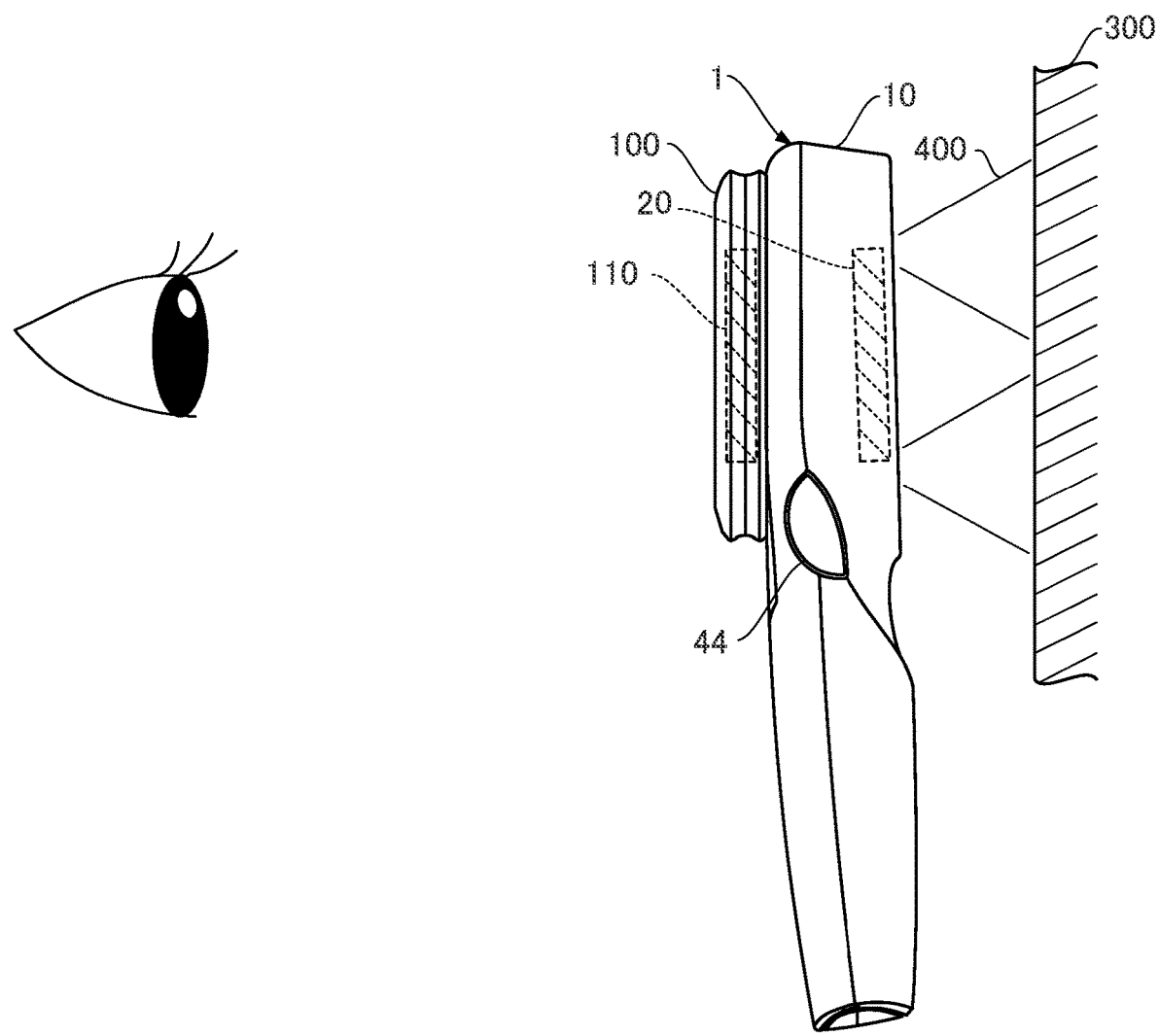
FIG. 13A is a drawing illustrating a situation in which the inspection device according to the embodiment of the present disclosure is being used with the conversion lens device attached, and is a schematic view illustrating a state of visible light exiting.
Figure 13B:
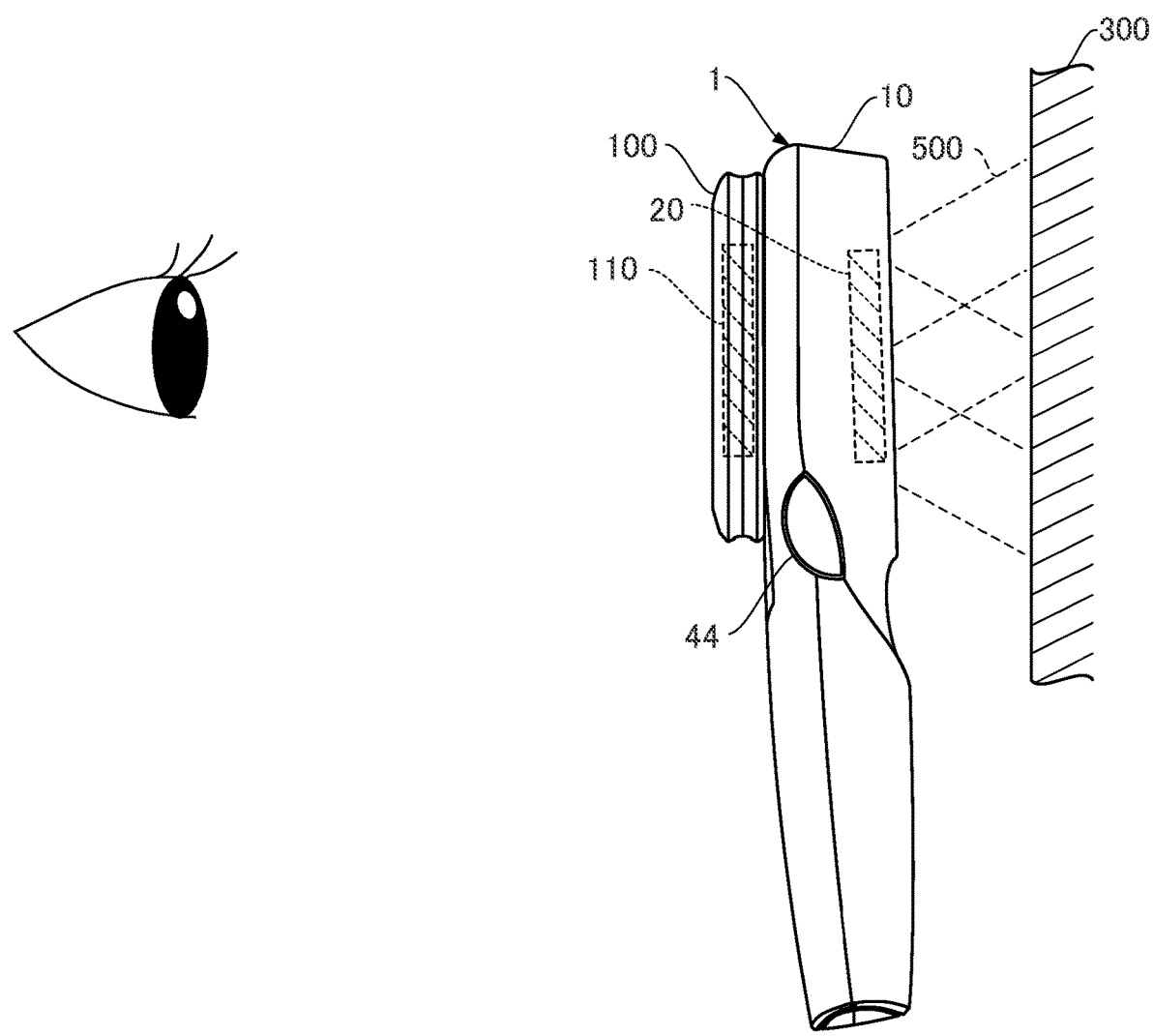
FIG. 13B is a drawing illustrating a situation in which the inspection device according to the embodiment of the present disclosure is being used with the conversion lens device attached, and is a schematic view illustrating a state of polarized visible light exiting.

As illustrated in FIGS. 13A and 13B, the inspection device 1 with the conversion lens device 100 attached is used when performing a dermoscopy inspection in which the skin is magnified further. Firstly, when the power of the inspection device 1 is not turned ON, the user presses the power button 44 to turn the power ON or, when the polarized light 500 is being emitted, press-operates the switch button 45 illustrated in FIG. 3 and causes the visible light 400 to be emitted from the inspection device 1. Then, the user brings the inspection device 1 close to the skin 300 and irradiates the skin 300 with the visible light 400. Then, as illustrated in FIG. 13A, the user secures a suitable distance between the skin 300 and the inspection device 1, and observes the skin 300 that is irradiated with the visible light 400. Thus, the user can observe, through the master lens 20 and the conversion lens 110, the condition of the surface stratum corneum of the skin 300 that is further magnified When the inspection of the skin 300 using the visible light 400 is complete, next, the user presses the switch button 45 illustrated in FIG. 3, and switches the light source that emits the light. As a result, the polarized visible light 500 is emitted from the inspection device 1. Then, the user brings the inspection device 1 close to the skin 300 and irradiates the skin 300 with the polarized visible light 500. Then, as illustrated in FIG. 13B, the user secures a suitable distance between the skin 300 and the inspection device 1, and observes the skin 300 that is irradiated with the polarized visible light 500. Thus, the user can observe, through the master lens 20 and the conversion lens 110, the conditions of the epidermis and the superficial dermis, which are deeper than the surface stratum corneum, of the skin 300 in a further magnified state.

Effects

According to the embodiment described above, the attaching of the conversion lens device 100 to the device main body 10 is carried out using the force (magnetic force) pulling the metal piece 34 provided on the device main body 10 and the permanent magnet 130 provided on the conversion lens device 100 toward each other. As such, the need for complex work when attaching and detaching the conversion lens device 100 is eliminated, and the attaching/detaching work of the conversion lens device 100 can be facilitated.

As illustrated in FIG. 5, the metal piece 34 is provided on the inclined surface 31b of the device main body 10, and is arranged inclined such that the normal line N1 of the main surface 34a of the metal piece 34 approaches (but is not parallel to) the optical axis OA1 of the master lens 20. By disposing the metal piece 34 inclined in this manner, the outer diameter R1 of the metal piece 34 can be made smaller while maintaining the attractive force of the permanent magnet 130 compared to a case in which a metal piece of the same area that is arranged such that the main surface of that metal piece is orthogonal to the optical axis OA1 is used. As such, in the device main body 10, the planar dimension (in this case, the dimensions in the X-Y plane) can be reduced and miniaturization of the device main body 10 can be realized. Additionally, since the outer diameter R1 of the metal piece 34 can be reduced, the region of the contact surface 31a illustrated in FIG. 6 formed along the outer periphery of the metal piece 34 can be made smaller As such, the structure for attaching the conversion lens can be made compact.

As illustrated in FIG. 8, the permanent magnet 130 is arranged inclined such that the normal line N2 of the main surface 130a moves away from (so as not to be parallel to) the optical axis OA2 of the conversion lens 110. By disposing the permanent magnet 130 inclined in this manner, compared to a case in which the permanent magnet 130 is arranged so as to be orthogonal to the optical axis OA2 of the conversion lens 110, the planar dimensions of the conversion lens device 100 (in this case, the dimensions in the X-Y plane) can be made smaller while maintaining the attractive force of the magnet. As such, the structure for attaching the conversion lens can be made compact, and the miniaturization of the conversion lens device 100 can be realized.

Figure 10:
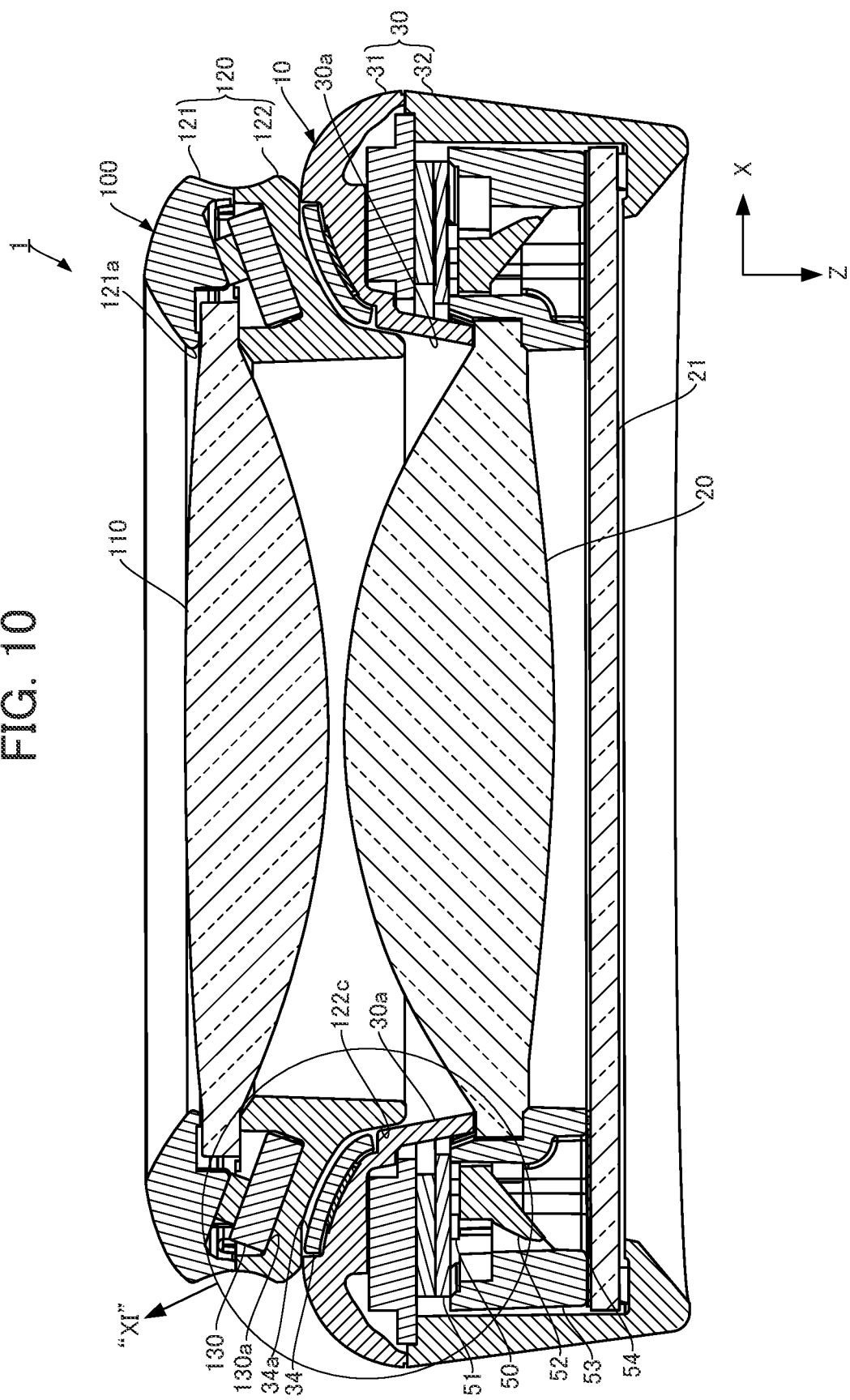
FIG. 10 is a drawing illustrating the inspection device according to the embodiment of the present disclosure, and is a cross-sectional view of a state in which the conversion lens device is attached.

As illustrated in FIG. 10, the metal piece 34 and the permanent magnet 130 are arranged such that at least a portion of the main surface 130a of the permanent magnet 130 and the main surface 34a of the metal piece 34 are substantially parallel. Due to this, sufficient force pulling the main surface 34a and the main surface 130a toward each other can be caused to act. As a result, increases in the size of the inspection device 1 can be suppressed and, at the same time, sufficient holding force when attaching the conversion lens device 100 to the device main body 10 can be secured.

As illustrated in FIG. 1 the metal piece 34 made from stainless steel is attached around the insertion part 30a of the case body 30 made from synthetic resin. Since the device main body 10 is formed from members of different materials in this manner, the design of the device main body 10 can be enhanced.

As illustrated in FIG. 6, the main surface 34a of the metal piece 34 is provided at a position the step H lower than (position on the +Z-axis direction side of) the contact surface 31a of the first case 31. Furthermore, as illustrated in FIG. 11, the contact avoider 122b of the second case 122 is shaped so as to avoid contact with the metal piece 34. Due to this, a gap can be formed between the conversion lens device 100 and the metal piece 34, and contact between the conversion lens device 100 and the metal piece 34 can be avoided. As a result, it is possible to prevent scratches from forming and debris from depositing on the metal piece 34 provided on the device main body 10, and the beauty of the device main body 10 can be maintained Additionally, since damage to the metal piece 34 can be suppressed, the attractive force of the permanent magnet 130 can be maintained and the durability of the inspection device 1 can be improved.

The conversion lens device 100 is provided with the protrusion 122c that is inserted into the insertion part 30a when attaching the conversion lens device 100 to the device main body 10. Due to this, when attaching the conversion lens device 100 to the device main body 10, the conversion lens device 100 is attached to the device main body 10 by simply inserting the protrusion 122c into the insertion part 30a, and is held thereafter by magnetic force. As such, the attaching work of the conversion lens device 100 can be performed simply, quickly, and reliably.

Since the protrusion 122c is inserted into the insertion part 30a of the device main body 10, further shifting of the conversion lens device 100 with respect to the device main body 10 can be prevented by the protrusion 122c contacting the insertion part 30a, even when a force acts to shift the conversion lens device 100 on the X-Y plane (on the plane orthogonal to the optical axis OA2) with respect to the device main body 10. That is, the protrusion 122c and the insertion part 30a act as movement limiting means that limit movement parallel to the X-Y plane of the conversion lens device 100.

With the device main body 10, light is emitted from the surface on the +Z-axis direction side where the skin that is the object to be inspected is arranged, and the conversion lens device 100 attaches/detaches to/from the surface on the-Z-axis direction side that is the surface of the opposite side. Due to this, malfunctions such as the conversion lens device 100 attached to the device main body 10 detaching and falling off do not occur, even when an inspection posture such as when the skin is arranged below and observation is performed from above is used. Additionally, since the conversion lens device 100 can be attached/detached while the light is being emitted to observe the skin, it is possible to smoothly carry out dermoscopy inspections that involve switching between the first state and the second state.

By passing a strap through the strap attacher 126 provided on the conversion lens device 100 and the strap attacher 43 provided on the device main body 10 illustrated in FIG. 1, it is possible to always carry the conversion lens device 100 and the device main body 10 together. As a result, dermoscopy inspections can be performed smoothly.

Modified Examples

The present disclosure is not limited to the embodiment described above, and various modifications and uses are possible. Any type of magnetic body can be attached to the device main body 10 and the conversion lens device 100. For example, a configuration is possible in which a metal piece to which a permanent magnet is attracted is provided on the conversion lens device 100, and a permanent magnet is provided on the device main body 10, the opposite of the case of the embodiment described above. Additionally, a configuration is possible in which a permanent magnet is provided on both the device main body 10 and the conversion lens device 100, and the permanent magnet of the device main body 10 and the permanent magnet of the conversion lens device 100 pull toward each other. Moreover, the metal piece 34 is not limited to being made from stainless steel, and may be a ferromagnetic material member such as cobalt, nickel, or the like.

A description is given in which the device main body 10 includes a light source that emits visible light and a light source that emits polarized visible light, but the device main body 10 may include any type of light source. For example, a configuration is possible in which a light source that emits ultraviolet light is provided, or a light source that emits near infrared light is provided. Additionally, the light emitted from the LEDs passes through a polarizing plate to obtain the polarized light, but a configuration is possible in which a polarizing film is attached to the LEDs to emit polarized light. Moreover, the light sources are not limited to LEDs, and a configuration is possible in which another light source, such as a fluorescent lamp, a mercury lamp, or an electroluminescence lamp, is used.

In the embodiment described above, a description is given of a case in which one conversion lens device 100 is attached/detached to/from the device main body 10. However, for example, a configuration is possible in which a plurality of conversion lens devices having conversion lenses of differing magnification factors is prepared, and the conversion lens device to be attached is selected in accordance with the magnification factor of the skin to be checked.

In the embodiment described above, an example is described in which the inspection device 1 to which the present disclosure is applied is a dermoscope for inspecting the skin. However, the present disclosure can be applied to other inspection devices. For example, the present disclosure can be applied to another device for inspecting the human body such as the ears, nostrils, oral cavity, and cervix.

Furthermore, the present disclosure can be applied to magnifying glasses for inspecting industrial products and magnifying glasses for inspecting structures.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled. Hereinafter, the invention disclosed in the claims of the present application as originally filed is recited.

This application claims the benefit of Japanese Patent Application No. 2020-016631, filed on Feb. 3, 2020, the entire disclosure of which is incorporated by reference herein.

INDUSTRIAL APPLICABILITY

The present disclosure is particularly useful for attaching a conversion lens to a device main body.

REFERENCE SIGNS LIST

1 Inspection device
10 Device main body
20 Master lens
20a Outer periphery
21 Cover plate
21a Outer periphery
30 Case body
30a Insertion part
30b Opening
31 First case
31a Contact surface
31b Inclined surface
31c Inclined wall
32 Second case
32a Opening
33 Double-sided tape
34 Metal piece
34a Main surface
35a Expanding section
35b Semicircle section
36a Expanding section
36b Semicircle section
40 Battery
41 Circuit board
42 Recharging terminal
43 Strap attacher
44 Power button
45 Switch button
50 LED
51 LED substrate
52 Light guide
53 Housing
53a Opening
54 Polarizing plate
54a Notch
54b Inner edge
100 Conversion lens device
110 Conversion lens
110a Outer edge
120 Lens frame
121 First case
121a Opening
122 Second case
122a Contactor
122b Contact avoider
122c Protrusion
122d Outer peripheral surface
123 Inclined surface
124 Opening
125 Indentation
126 Strap attacher
130 Permanent magnet
130a Main surface
150 Contact region
300 Skin
400 Visible light
500 Polarized visible light

The invention claimed is:

1. A conversion lens attachment structure, comprising:
a first magnetic body provided on a conversion lens device that includes a conversion lens; and
a second magnetic body provided on a device main body that includes a master lens,
wherein:
the conversion lens device is configured to be held in a state in which the conversion lens device is attached to the device main body due to an attraction effect between a first surface of the first magnetic body and a second surface of the second magnetic body,
a contact surface that closely contacts the conversion lens device due to the attraction effect, and an insertion part into which the conversion lens device is to be inserted, are provided to the device main body,
the conversion lens device includes:
a contactor that contacts the contact surface and that is arranged to be on an outer periphery of the device main body outward from the second magnetic body, and
a contact avoider that is provided more to an optical axis side of the conversion lens than the contactor, and that is formed so as to avoid contact with the second magnetic body, and
the second magnetic body is provided between the contact surface and the insertion part of the device main body, and is provided such that a normal line of the second surface is not parallel to an optical axis of the master lens.

2. The conversion lens attachment structure according to claim 1, wherein the first magnetic body is arranged such that at least a portion of the first surface is substantially parallel to the second surface of the second magnetic body.

3. The conversion lens attachment structure according to claim 1, wherein:
the conversion lens device includes a lens frame that holds the conversion lens, and
a plurality of the first magnetic body are arranged in the lens frame so as to correspond to the second magnetic body.

4. The conversion lens attachment structure according to claim 1, wherein a region of the contact surface that contacts the contactor is subjected to surface texturing.

5. The conversion lens attachment structure according to claim 1, wherein the first magnetic body includes a permanent magnet.

6. The conversion lens attachment structure according to claim 1, wherein the second magnetic body includes a metal piece made of stainless steel.

7. A conversion lens attachment structure, comprising:
a first magnetic body provided on a conversion lens device that includes a conversion lens; and
a second magnetic body provided on a device main body that includes a master lens,
wherein:
the conversion lens device is configured to be held in a state in which the conversion lens device is attached to the device main body due to an attraction effect between a first surface of the first magnetic body and a second surface of the second magnetic body,
a contact surface that closely contacts the conversion lens device due to the attraction effect, and an insertion part into which the conversion lens device is to be inserted, are provided to the device main body,
the second magnetic body is provided between the contact surface and the insertion part of the device main body, and is provided such that a normal line of the second surface is not parallel to an optical axis of the master lens, and
a protrusion, which has a cylindrical shape and which is inserted into the insertion part having a circular shape when the conversion lens device is attached to the device main body, is provided on the conversion lens device.

8. An inspection device comprising:
a conversion lens device including a conversion lens;
a device main body including a master lens; and
a conversion lens attachment structure including a first magnetic body provided on the conversion lens device and a second magnetic body provided on the device main body,
wherein:
the inspection device is configured to inspect an object to be inspected through at least the master lens,
the device main body further includes a first light source that irradiates with visible light the object to be inspected, and a second light source that irradiates with polarized visible light the object to be inspected,
the conversion lens device is configured to be held in a state in which the conversion lens device is attached to the device main body due to an attraction effect between a first surface of the first magnetic body and a second surface of the second magnetic body, and
the second magnetic body is provided such that a normal line of the second surface is not parallel to an optical axis of the master lens.

9. The inspection device according to claim 8, wherein the first light source and the second light source emit light from a side of the device main body on which the object to be inspected is positioned, the side being opposite a side on which the conversion lens device is attached.

10. The inspection device according to claim 8, wherein the first light source and the second light source are arranged around the master lens.

11. A conversion lens attachment structure, comprising:
a first magnetic body provided on a conversion lens device that includes a conversion lens; and
a second magnetic body provided on a device main body that includes a master lens,
wherein:
the conversion lens device is configured to be held in a state in which the conversion lens device is attached to the device main body due to an attraction effect between a first surface of the first magnetic body and a second surface of the second magnetic body, and
the second magnetic body is provided such that a normal line of the second surface intersects an optical axis of the master lens at an angle that is neither parallel nor perpendicular to the optical axis.

* * * * *